(12) United States Patent
Haviv et al.

(10) Patent No.: US 7,037,897 B2
(45) Date of Patent: May 2, 2006

(54) TRI-, TETRA-, AND PENTA-PEPTIDES HAVING ANTIANGIOGENIC ACTIVITY

(75) Inventors: Fortuna Haviv, Deerfield, IL (US); Michael F. Bradley, Wadsworth, IL (US)

(73) Assignee: Abbott Laboratories, Abbott Park, IL (US)

( * ) Notice: Subject to any disclaimer, the term of this patent is extended or adjusted under 35 U.S.C. 154(b) by 436 days.

(21) Appl. No.: 10/283,813

(22) Filed: Oct. 30, 2002

(65) Prior Publication Data

US 2003/0109456 A1 Jun. 12, 2003

Related U.S. Application Data

(60) Provisional application No. 60/335,018, filed on Oct. 31, 2001.

(51) Int. Cl.
*A61K 38/00* (2006.01)
(52) U.S. Cl. ............................. 514/17; 514/16; 530/329
(58) Field of Classification Search .................. 514/16, 514/17; 530/329
See application file for complete search history.

(56) References Cited

U.S. PATENT DOCUMENTS

2003/0105022 A1 * 6/2003 Haviv et al. .................. 514/16

FOREIGN PATENT DOCUMENTS

| JP | 05-306295 | * 4/1992 |
| JP | 05-306295 | 11/1993 |
| WO | 99/61476 | 12/1999 |
| WO | 01/38347 | 5/2001 |
| WO | 01/38397 | 5/2001 |

* cited by examiner

*Primary Examiner*—Bruce R. Campell
*Assistant Examiner*—Roy Teller
(74) *Attorney, Agent, or Firm*—Johanna M. Corbin; Gregory W. Steele

(57) ABSTRACT

Compounds of formula (SEQ ID NO:1), which are useful for treating conditions that arise from or are exacerbated by angiogenesis, are described. Also disclosed are pharmaceutical compositions comprising these compounds, methods of treatment using these compounds, and methods of inhibiting angiogenesis.

13 Claims, No Drawings

TRI-, TETRA-, AND PENTA-PEPTIDES HAVING ANTIANGIOGENIC ACTIVITY

This application claims priority to U.S. Provisional Patent Application Ser. No. 60/335,018, filed on Oct. 31, 2001, which is hereby incorporated by reference.

TECHNICAL FIELD

The present invention relates to methods of inhibiting angiogenesis, methods of treating cancer, and compounds having activity useful for treating conditions which arise from or are exacerbated by angiogenesis. Also disclosed are pharmaceutical compositions comprising the compounds and methods of treatment using the compounds.

BACKGROUND OF THE INVENTION

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions these molecules appear to maintain the microvasculature in a quiescent state (i.e., one of no capillary growth) for prolonged periods that may last for weeks, or in some cases, decades. However, when necessary, such as during wound repair, these same cells can undergo rapid proliferation and turnover within as little as five days.

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition. For example, the growth and metastasis of solid tumors have been shown to be angiogenesis-dependent. Based on these findings, there is a continuing need for compounds which demonstrate antiangiogenic activity due to their potential use in the treatment of various diseases such as cancer. Peptides having angiogenesis inhibiting properties have been described in commonly-owned WO01/38397, WO01/38347, WO99/61476, and U.S. patent application Ser. No. 09/915,956. However, it would be desirable to prepare antiangiogenic compounds having improved profiles of activity and smaller size.

SUMMARY OF THE INVENTION

The present invention relates to a novel class of compounds having angiogenesis-inhibiting properties. The invention provides peptides with enhanced properties of angiogenesis inhibition. In its principle embodiment, the present invention provides a compound of formula (I)

$$\text{Xaa}_1\text{-Xaa}_2\text{-Xaa}_3\text{-Xaa}_4\text{-Xaa}_5\text{-Xaa}_6 \text{ (SEQ ID NO:1)} \quad (I),$$

or a therapeutically acceptable salt thereof, wherein $\text{Xaa}_1$ is selected from the group consisting of hydrogen and $R-(CH_2)_n-C(O)-$, wherein n is an integer from 0 to 8 and R is selected from the group consisting of alkoxy, alkyl, amino, aryl, carboxyl, cycloalkenyl, cycloalkyl, and heterocycle;

$\text{Xaa}_2$ is selected from the group consisting of N-methylalanyl, allothreonyl, allylglycyl, arginyl, beta-alanyl, glutaminyl, D-glutaminyl, glycyl, homoseryl, leucyl, lysyl (N-epsilon acetyl), norleucyl, norvalyl, D-norvalyl, N-methylnorvalyl, ornithyl(N-delta acetyl), 3-(3-pyridyl)alanyl, sarcosyl, seryl, D-seryl, N-methylseryl, threonyl, tryptyl, D-tryptyl, valyl, and N-methylvalyl;

$\text{Xaa}_3$ is selected from the group consisting of alanyl, alloisoleucyl, aspartyl, citrullyl, isoleucyl, D-isoleucyl, N-methylisoleucyl, leucyl, D-leucyl, lysyl(N-epsilon acetyl), D-lysyl(N-epsilon acetyl), norvalyl, phenylalanyl, prolyl, and D-prolyl;

$\text{Xaa}_4$ is selected from the group consisting of arginyl, D-arginyl, citrullyl, histidyl, isoleucyl, lysyl, lysyl(N-epsilon isopropyl), ornithyl, and 3-(3-pyridyl)alanyl;

$\text{Xaa}_5$ is absent or selected from the group consisting of N-methyl-D-alanyl, 2-aminobutyryl, 2-aminoisobutyryl, arginyl, D-glutaminyl, homoprolyl, hydroxyprolyl, leucyl, phenylalanyl, prolyl, D-prolyl, and D-valyl;

provided that when $\text{Xaa}_4$ is arginyl or D-arginyl then $\text{Xaa}_5$ is other than arginyl; and $\text{Xaa}_6$ is selected from the group consisting of hydroxyl, D-alanylamide, azaglycylamide, glycylamide, D-lysyl(N-epsilon acetyl)amide, prolylethylamide, $-NHCH(CH_3)_2$, a group represented by the formula $-NH-(CH_2)_n-CHR^1R^2$, and a group represented by the formula $-NHR^3$, wherein n is an integer from 0 to 8; $R^1$ is selected from the group consisting of hydrogen, alkyl, cycloalkenyl, and cycloalkyl; $R^2$ is selected from the group consisting of hydrogen, alkoxy, alkyl, aryl, cycloalkenyl, cycloalkyl, heterocycle, and hydroxyl, with the proviso that when n is 0, $R^2$ is other than alkoxy or hydroxyl; and $R^3$ is selected from the group consisting of hydrogen, cycloalkenyl, cycloalkyl, and hydroxyl.

In another embodiment, the present invention provides a pharmaceutical composition comprising a compound of formula (I), or a therapeutically acceptable salt thereof, in combination with a therapeutically acceptable carrier.

In another embodiment, the present invention provides a method of inhibiting angiogenesis in a mammal in recognized need of such treatment comprising administering to the mammal a therapeutically acceptable amount of a compound of formula (I), or a therapeutically acceptable salt thereof.

In another embodiment, the present invention provides a method of treating cancer in a mammal in recognized need of such treatment comprising administering to the mammal a therapeutically acceptable amount of a compound of claim 1 or a therapeutically acceptable salt thereof.

DETAILED DESCRIPTION OF THE INVENTION

In another embodiment, the present invention relates to compounds of formula (I) wherein $\text{Xaa}_4$ is arginyl; and $\text{Xaa}_1$, $\text{Xaa}_2$, $\text{Xaa}_3$, $\text{Xaa}_5$, and $\text{Xaa}_6$ are as defined in formula (I).

In another embodiment, the present invention relates to compounds of formula (I) wherein $\text{Xaa}_2$ is selected from the group consisting of norvalyl and D-norvalyl; $\text{Xaa}_4$ is arginyl; and $\text{Xaa}_1$, $\text{Xaa}_3$, $\text{Xaa}_5$, and $\text{Xaa}_6$ are as defined in formula (I).

In another embodiment, the present invention relates to compounds of formula (I) wherein $\text{Xaa}_2$ is selected from the group consisting of glutaminyl, D-glutaminyl, leucyl, norleucyl, D-seryl, and seryl; $\text{Xaa}_4$ is arginyl; and $\text{Xaa}_1$, $\text{Xaa}_3$, $\text{Xaa}_5$, and $\text{Xaa}_6$ are as defined in formula (I).

In another embodiment, the present invention relates to compounds of formula (I) wherein $\text{Xaa}_2$ is selected from the group consisting of allothreonyl, allylglycyl, arginyl, glycyl, lysyl(N-epsilon acetyl), threonyl, D-tryptyl, and tryptyl; Xaa$_4$ is arginyl; and Xaa$_1$, Xaa$_3$, Xaa$_5$, and Xaa$_6$ are as defined in formula (I).

In another embodiment, the present invention relates to compounds of formula (I) wherein Xaa$_5$ is arginyl; and Xaa$_1$, Xaa$_2$, Xaa$_3$, Xaa$_4$, and Xaa$_6$ are as defined in formula (I).

In another embodiment, the present invention relates to compounds of formula (I) wherein Xaa$_2$ is beta-alanyl; Xaa$_5$ is arginyl; and Xaa$_1$, Xaa$_3$, Xaa$_4$, and Xaa$_6$ are as defined in formula (I).

In another embodiment, the present invention relates to compounds of formula (I) wherein Xaa$_1$ is R—(CH$_2$)$_n$—C(O)—, wherein n is 0 and R is an alkyl group wherein a preferred alkyl group is methyl; Xaa$_2$ is selected from the group consisting of allylglycyl, arginyl, beta-alanyl, norleucyl, leucyl, lysyl(N-epsilon-acetyl), glycyl, glutaminyl, D-glutaminyl, norvalyl, D-norvalyl, seryl, D-seryl, allothreonyl, threonyl, tryptyl, and D-tryptyl; Xaa$_3$ is selected from the group consisting of citrullyl, isoleucyl, D-isoleucycl, lysyl(N-epsilon-acetyl), norvalyl, and prolyl; Xaa$_4$ is selected from the group consisting of arginyl and isoleucyl; Xaa$_5$ is absent or selected from the group consisting of prolyl and arginyl; and Xaa$_6$ is selected from the group consisting of —NHCH$_2$CH$_3$, —NHCH(CH$_3$)$_2$, prolylethylamide, and D-alanylamide.

In another embodiment, the present invention relates to compounds of formula (I) wherein Xaa$_1$ is R—(CH$_2$)$_n$—C(O)—, wherein n is 0 and R is heterocycle wherein a preferred heterocycle is 6-methylpyridinyl; Xaa$_2$ is selected from the group consisting of allylglycyl, arginyl, beta-alanyl, norleucyl, leucyl, lysyl(N-epsilon-acetyl), glycyl, glutaminyl, D-glutaminyl, norvalyl, D-norvalyl, seryl, D-seryl, allothreonyl, threonyl, tryptyl, and D-tryptyl; Xaa$_3$ is selected from the group consisting of citrullyl, isoleucyl, D-isoleucycl, lysyl(N-epsilon-acetyl), norvalyl, and prolyl; Xaa$_4$ is selected from the group consisting of arginyl and isoleucyl; Xaa$_5$ is absent or selected from the group consisting of prolyl and arginyl; and Xaa$_6$ is selected from the group consisting of —NHCH$_2$CH$_3$, —NHCH(CH$_3$)$_2$, prolylethylamide, and D-alanylamide.

In another embodiment, the present invention relates to compounds of formula (I) wherein Xaa$_3$ is isoleucyl; Xaa$_4$ is arginyl; Xaa$_5$ is prolyl; and Xaa$_1$, Xaa$_2$ and Xaa$_6$ are as defined in formula (I).

In another embodiment, the present invention relates to compounds of formula (I) wherein Xaa$_3$ is isoleucyl; Xaa$_4$ is arginyl; Xaa$_5$ is prolyl; and Xaa$_6$ is selected from the group consisting of —NHCH$_2$CH$_3$, —NHCH(CH$_3$)$_2$, and D-alanylamide; and Xaa$_1$ and Xaa$_2$ are as defined in formula (I).

In another embodiment, the present invention relates to compounds of formula (I) wherein Xaa$_1$ is R—(CH$_2$)$_n$—C(O)—, wherein n is 0 and R is an alkyl group wherein a preferred alkyl group is methyl; Xaa$_2$ is selected from the group consisting of allylglycyl, arginyl, beta-alanyl, norleucyl, leucyl, lysyl(N-epsilon-acetyl), glycyl, glutaminyl, D-glutaminyl, norvalyl, D-norvalyl, seryl, D-seryl, allothreonyl, threonyl, tryptyl, and D-tryptyl; Xaa$_3$ is isoleucyl; Xaa$_4$ is arginyl; Xaa$_5$ is prolyl; and Xaa$_6$ is selected from the group consisting of —NHCH$_2$CH$_3$, —NHCH(CH$_3$)$_2$, and D-alanylamide.

In another embodiment, the present invention relates to compounds of formula (I) wherein Xaa$_1$ is R—(CH$_2$)$_n$—C(O)—, wherein n is 0 and R is an alkyl group wherein a preferred alkyl group is methyl; Xaa$_2$ is selected from the group consisting of allylglycyl, arginyl, beta-alanyl, norleucyl, leucyl, lysyl(N-epsilon-acetyl), glycyl, glutaminyl, D-glutaminyl, norvalyl, D-norvalyl, seryl, D-seryl, allothreonyl, threonyl, tryptyl, and D-tryptyl; Xaa$_3$ is selected from the group consisting of citrullyl, isoleucyl, D-isoleucycl, lysyl(N-epsilon-acetyl), norvalyl, and prolyl; Xaa$_4$ is selected from the group consisting of arginyl and isoleucyl; Xaa$_5$ is absent; and Xaa$_6$ is selected from the group consisting of —NHCH$_2$CH$_3$, —NHCH(CH$_3$)$_2$, and D-alanylamide.

Definitions

As used herein, the singular forms "a", "an", and "the" include plural reference unless the context clearly dictates otherwise.

As used in the present specification the following terms have the meanings indicated:

The term "alkoxy," as used herein, represents an alkyl group attached to the parent molecular moiety through an oxygen atom.

The term "alkyl," as used herein, represents a monovalent group derived from a straight or branched chain saturated hydrocarbon by the removal of a hydrogen atom. Preferred alkyl groups for the present invention invention are alkyl groups having from one to six carbon atoms (C$_1$–C$_6$ alkyl). Alkyl groups of one to three carbon atoms (C$_1$–C$_3$ alkyl) are more preferred for the present invention.

The term "alkylcarbonyl," as used herein, represents an alkyl group attached to the parent molecular moiety through a carbonyl group.

The term "amino," as used herein, represents —NR$^a$R$^b$, wherein R$^a$ and R$^b$ are independently selected from the group consisting of hydrogen, alkyl, and alkylcarbonyl.

The term "aryl," as used herein, represents a phenyl group, or a bicyclic or tricyclic fused ring system wherein one or more of the fused rings is a phenyl group. Bicyclic fused ring systems are exemplified by a phenyl group fused to a cycloalkenyl group, as defined herein, a cycloalkyl group, as defined herein, or another phenyl group. Tricyclic fused ring systems are exemplified by a bicyclic fused ring system fused to a cycloalkenyl group, as defined herein, a cycloalkyl group, as defined herein or another phenyl group. Representative examples of aryl include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkoxy, alkyl, carboxyl, halo, and hydroxyl.

The term "carbonyl," as used herein, represents —C(O)—.

The term "carboxyl," as used herein, represents —CO$_2$H.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Examples of cycloalkenyl groups include cyclohexenyl, octahydronaphthalenyl, norbomylenyl, and the like. The cycloalkenyl groups of the present invention can be optionally substituted with one, two, three, four, or five substituents independently selected from the group consisting of alkoxy, alkyl, carboxyl, halo, and hydroxyl.

The term "cycloalkyl," as used herein, refers to a saturated monocyclic, bicyclic, or tricyclic hydrocarbon ring system having three to twelve carbon atoms. Examples of cycloalkyl groups include cyclopropyl, cyclopentyl, bicyclo[3.1.1]heptyl, adamantyl, and the like. The cycloalkyl groups of the present invention can be optionally substituted with one, two, three, four, or five substituents independently selected from the group consisting of alkoxy, alkyl, carboxyl, halo, and hydroxyl.

The term "halo," as used herein, represents F, Cl, Br, or I.

The term "heterocycle," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocycle" also includes bicyclic groups in which the heterocycle ring is fused to an aryl group, as defined herein. The heterocycle groups of the present invention can be attached through a carbon atom or a nitrogen atom in the group. Examples of heterocycles include, but are not limited to, furyl, thienyl, pyrrolyl, pyrrolidinyl, oxazolyl, thiazolyl, imidazolyl, imidazolinyl, pyrazolyl, isoxazolyl, isothiazolyl, piperidinyl, morpholinyl, thiomorpholinyl, piperazinyl, pyridinyl, indolyl, indolinyl, benzothienyl, and the like. The heterocycle groups of the present invention can be optionally substituted with one, two, three, or four substituents independently selected from the group consisting of alkoxy, alkyl, carboxyl, halo, and hydroxyl.

The term "hydroxyl," as used herein, represents —OH.

The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate,trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Unless indicated otherwise by a "D" prefix, e.g., D-Ala or NMe-D-Ile, the stereochemistry of the α-carbon of the amino acids and aminoacyl residues in peptides described in this specification and the appended claims is the natural or "L" configuration. The Cahn-Ingold-Prelog "R" and "S" designations are used to specify the stereochemistry of chiral centers in certain acyl substituents at the N-terminus of the peptides of this invention. The designation "R,S" is meant to indicate a racemic mixture of the two enantiomeric forms. This nomenclature follows that described in R. S. Cahn, et al., *Angew. Chem. Int. Ed. Engl.*, 5, 385–415 (1966).

All peptide sequences are written according to the generally accepted convention whereby the α-N-terminal amino acid residue is on the left and the α-C-terminal is on the right. As used herein, the term "α-N-terminus" refers to the free α-amino group of an amino acid in a peptide, and the term "α-C-terminus" refers to the free α-carboxylic acid terminus of an amino acid in a peptide.

For the most part, the names on naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)"*Biochemistry*, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

| Abbreviation | Definition |
| --- | --- |
| Ala | alanyl |
| AlaNH$_2$ | alanylamide |
| alloThr | allothreonyl |
| alloThr(t-Bu) | allothreonyl(O-t-butyl) |
| allylGly | allylglycyl |
| Arg | arginyl |
| Arg-NHCH$_2$CH$_3$ | arginylethylamide |
| Arg-NHCH(CH$_3$)$_2$ | arginylisopropylamide |
| Arg(Pmc) | arginyl(N$^G$-2,2,5,7,8-pentamethylchroman-6-sulfonyl) |
| Arg(Pbf) | N$^G$-(2,2,4,6,7-pentamethyldihydrobenzofuran-5-sulfonyl)arginine |
| Asp | aspartyl |
| bAla | beta-alanyl |
| Cit | citrullyl |
| Fmoc | 9-fluorenylmethyloxycarbonyl |
| Gln | glutaminyl |
| Gln(Trt) | glutaminyl(trityl) |
| Gly | glycyl |
| His | histidyl |
| Hser | homoseryl |
| Ile | isoleucyl |
| aIle | alloisoleucyl |
| Leu | leucyl |
| Lys | lysyl |
| Lys(Ac) | lysyl(N-epsilon-acetyl) |
| Nle | norleucyl |
| Nva | norvalyl |
| NMeNva | N-methylnorvalyl |
| Orn | ornithyl |
| Orn(Ac) | ornithyl(N-delta-acetyl) |
| 3-Pal | 3-(3-pyridyl)alanyl |
| Phe | phenylalanyl |
| Pro | prolyl |
| Pro-NHCH$_2$CH$_3$ | prolylethylamide |
| Pro-NHCH(CH$_3$)$_2$ | prolylisopropylamide |
| Sar | sarcosyl |
| Ser | seryl |
| Ser(t-Bu) | seryl(O-t-butyl) |
| Thr | threonyl |
| Thr(t-Bu) | threonyl(O-t-butyl) |
| Trp | tryptyl |
| Trp(Boc) | tryptyl(tert-butoxycarbonyl) |
| Val | valyl |

When not found in the table above, nomenclature and abbreviations may be further clarified by reference to the Calbiochem-Novabiochem Corp. 1999 *Catalog and Peptide*

*Synthesis Handbook* or the Chem-Impex International, Inc. *Tools for Peptide & Solid Phase Synthesis* 1998–1999 *Catalogue*.

Compositions

The compounds of the invention, including not limited to those specified in the examples, possess anti-angiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungosides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including not limited to intestinal adhesions, Crohn's disease, atherosclerosis, scleroderma, and hypertrophic scars, i.e., keloids. Another use is as a birth control agent, by inhibiting ovulation and establishment of the placenta. The compounds of the invention are also useful in the treatment of diseases that have angiogenesis as a pathologic consequence such as cat scratch disease (*Rochele minutesalia quintosa*) and ulcers (*Helicobacter pylori*). The compounds of the invention are also useful to reduce bleeding by administration prior to surgery, especially for the treatment of resectable tumors.

The compounds of the invention may be used in combination with other compositions and procedures for the treatment of diseases. For example, a tumor may be treated conventionally with surgery, radiation or chemotherapy combined with a peptide of the present invention and then a peptide of the present invention may be subsequently administered to the patient to extend the dormancy of micrometastases and to stabilize and inhibit the growth of any residual primary tumor. Additionally, the compounds of the invention may be combined with pharmaceutically acceptable excipients, and optionally sustained-release matrices, such as biodegradable polymers, to form therapeutic compositions.

A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho) esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

When used in the above or other treatments, a therapeutically effective amount of one of the compounds of the present invention may be employed in pure form or, where such forms exist, in pharmaceutically acceptable salt form. By a "therapeutically effective amount" of the compound of the invention is meant a sufficient amount of the compound to treat an angiogenic disease, (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved.

Alternatively, a compound of the present invention may be administered as pharmaceutical compositions containing the compound of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions may be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters), poly(anhydrides), and (poly)glycols, such as PEG. Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds of the invention may be injected directly into the vitreous and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

While the compounds of the invention can be administered as the sole active pharmaceutical agent, they may also be used in combination with one or more agents which are conventionally administered to patients for treating angiogenic diseases. For example, the compounds of the invention are effective over the short term to make tumors more sensitive to traditional cytotoxic therapies such as chemicals and radiation. The compounds of the invention also enhance the effectiveness of existing cytotoxic adjuvant anti-cancer therapies. The compounds of the invention may also be combined with other antiangiogenic agents to enhance their effectiveness, or combined with other antiangiogenic agents and administered together with other cytotoxic agents. In particular, when used in the treatment of solid tumors, compounds of the invention may be administered with IL-12, retinoids, interferons, angiostatin, endostatin, thalidomide, thrombospondin-1, thrombospondin-2, captopryl, angioinhibins, TNP-470, pentosan polysulfate, platelet factor 4, LM-609, SU-5416, CM-101, Tecogalan, plasminogen-K-5, vasostatin, vitaxin, vasculostatin, squalamine, marimastat or other MMP inhibitors, anti-neoplastic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, cisplatin, taxol, etoposide/mechlorethamine, vincristine, prednisone and procarbazine), vincristine, vinblastine, and the like as well as with radiation.

Total daily dose of the compositions of the invention to be administered to a human or other mammal host in single or divided doses may be in amounts, for example, from 0.0001 to 300 mg/kg body weight daily and more usually 1 to 300 mg/kg body weight.

It will be understood that agents which can be combined with the compound of the present invention for the inhibition, treatment or prophylaxis of angiogenic diseases are not limited to those listed above, include in principle any agents useful for the treatment or prophylaxis of angiogenic diseases.

Determination of Biological Activity

In vitro Assay for Angiogenic Activity

The human microvascular endothelial cell (HMVEC) migration assay was run according to the procedure of S. S. Tolsma, O. V. Volpert, D. J. Good, W. F. Frazier, P. J. Polverini and N. Bouck, J. Cell Biol. 1993, 122, 497–511.

The HMVEC migration assay was carried out using Human Microvascular Endothelial Cells-Dermal (single donor) and Human Microvascular Endothelial Cells, (neonatal). The HMVEC cells were starved overnight in DME containing 0.01% bovine serum albuminutes (BSA). Cells were then harvested with trypsin and resuspended in DME with 0.01% BSA at a concentration of $1.5 \times 10^6$ cells per mL. Cells were added to the bottom of a 48 well modified Boyden chamber (Nucleopore Corporation, Cabin John, Md.). The chamber was assembled and inverted, and cells were allowed to attach for 2 hours at 37° C. to polycarbonate chemotaxis membranes (5 μm pore size) that had been soaked in 0.01% gelatin overnight and dried. The chamber was then reinverted, and test substances (total volume of 50 μL), including activators, 15 ng/mL bFGF/VEGF, were added to the wells of the upper chamber. The apparatus was incubated for 4 hours at 37° C. Membranes were recovered, fixed and stained (Diff Quick, Fisher Scientific) and the number of cells that had migrated to the upper chamber per 3 high power fields counted. Background migration to DME+0.1 BSA was subtracted and the data reported as the number of cells migrated per 10 high power fields (400×) or, when results from multiple experiments were combined, as the percent inhibition of migration compared to a positive control.

Representative compounds of the present invention inhibited human endothelial cell migration in the above assay by at least 50% when tested at a concentration of 1 nM. More preferred compounds inhibited human endothelial cell migration by approximately 70% to 90% when tested at a concentration of 1 nM, and most preferred compounds inhibited human endothelial cell migration by greater than 80% when tested at a concentration of 1 nM. As shown by these results, the compounds of the present invention demonstate an enhanced ability to inhibit angiogenesis as compared to previously described antiangiogenic compounds.

Synthesis of the Peptides

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

The polypeptides of the present invention may be synthesized by many techniques that are known to those skilled in the art. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

Reagents, resins, amino acids, and amino acid derivatives are commercially available and can be purchased from Chem-Impex International, Inc. (Wood Dale, Ill., U.S.A.) or Calbiochem-Novabiochem Corp. (San Diego, Calif., U.S.A.) unless otherwise noted herein.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis. In this particularly preferred method the α-amino function is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are 9-fluorenylmethyloxycarbonyl (Fmoc), t-butoxycarbonyl (Boc), benzyloxycarbonyl (Cbz), biphenylisopropyl-oxycarbonyl, t-amyloxycarbonyl, isobomyloxycarbonyl, (α,α)-dimethyl-3,5-dimethoxybenzyloxycarbonyl, O-nitrophenylsulfenyl, 2-cyano-t-butyloxycarbonyl, and the like. The 9-fluorenylmethyloxycarbonyl (Fmoc) protecting group is preferred.

Particularly preferred side chain protecting groups are: for arginine: $N^G$-2,2,5,7,8-pentamethylchroman-6-sulfonyl (Pmc), and 2,2,4,6,7-pentamethyldihydrobenzofuran-S-sulfonyl (Pbf); for glutamine: trityl (Trt); for serine: t-butyl (t-Bu); for allothreonine: t-butyl (t-Bu); and for tryptophan: t-butoxycarbonyl (Boc).

In the solid phase peptide synthesis method, the C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of C-terminal carboxyl peptides is Sieber amide resin or Sieber ethylamide resin. The preferred solid support for C-terminal amide peptides is Sieber ethylamide resin available from Novabiochem Corporation.

The C-terminal amino acid is coupled to the resin by means of a coupling mediated by N,N'-dicyclohexylcarbodiimide (DCC), N,N'-diisopropylcarbodiimide (DIC), [O-(7-azabenzotriazol-1-yl)-1,1,3,3-tetramethyluronium hexafluorophosphate] (HATU), or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), N-methylmorpholine (NMM), benzotriazol-1-yloxy-tris(dimethylamino)phosphonium-hexafluorophosphate (BOP) or bis(2-oxo-3-oxazolidinyl) phosphine chloride (BOPCl), for about 1 to about 24 hours at a temperature of between 10° C. and 50° C. in a solvent such as dichloromethane or DMF.

When the solid support is Sieber amide or Sieber ethylamide resin, the Fmoc group is cleaved with a secondary amine, preferably piperidine, prior to coupling with the C-terminal amino acid as described above. The preferred reagents used in the coupling to the deprotected 4-(2',4'-dimethoxyphenyl-Fmoc-aminomethyl)phenoxyacetamidoethyl resin are O-benzotriazol-1-yl-N,N,N',N'-tetramethyluroniumhexafluorophosphate (HBTU, 1 equiv.) with 1-hydroxybenzotriazole (HOBT, 1 equiv.), or [O-(7-azabenzotriazol-1-yl)-1,1,3,3-tetramethyluronium hexafluorophosphate] (HATU, 1 equiv.) with N-methylmorpholine (1 equiv.) in DMF.

The coupling of successive protected amino acids can be carried out in an automatic polypeptide synthesizer as is well known in the art. In a preferred embodiment, the α-amino function in the amino acids of the growing peptide chain are protected with Fmoc. The removal of the Fmoc protecting group from the N-terminal side of the growing peptide is accomplished by treatment with a secondary amine, preferably piperidine. Each protected amino acid is then introduced in about 3-fold molar excess and the coupling is preferably carried out in DMF. The coupling agent is normally O-benzotriazol-1-yl-N,N,N',N'-tetramethyluronium-hexafluorophosphate (HBTU, 1 equiv.) or [O-(7-azabenzotriazol-1-yl)-1,1,3,3-tetramethyluronium hexafluorophosphate] (HATU, 1 equiv.) in the presence of N-methylmorpholine (NMM, 1 equiv.).

At the end of the solid phase synthesis, the polypeptide is removed from the resin and deprotected, either in succession or in a single operation. Removal of the polypeptide and deprotection can be accomplished in a single operation by treating the resin-bound polypeptide with a cleavage reagent, for example trifluoroacetic acid containing thianisole, water, or ethanedithiol.

In cases where the C-terminus of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail-described above.

The fully deprotected peptide is purified by a sequence of chromatographic steps employing any or all of the following types: ion exchange on a weakly basic resin in the acetate form; hydrophobic adsorption chromatography on underivitized polystyrene-divinylbenzene (for example, AMBERLITE® XAD); silica gel adsorption chromatography; ion exchange chromatography on carboxymethylcellulose; partition chromatography, e.g., on SEPHADEX® G-25, LH-20 or countercurrent distribution; high performance liquid chromatography (HPLC), especially reverse-phase HPLC on octyl- or octadecylsilyl-silica bonded phase column packing.

The foregoing may be better understood in light of the examples which are meant to describe compounds and process which can be carried out in accordance with the invention and are not intended as a limitation on the scope of the invention in any way.

Abbreviations which have been used the following examples are: DMF for N,N-dimethylformamide; HBTU for O-benzotriazol-1-yl-N,N,N',N'-tetramethyluronium-hexafluorophosphate; NMM for N-methylmorpholine; and TFA for trifluoroacetic acid.

EXAMPLE 1

N-Ac-Nva-Ile-Arg-Pro-NHCH$_2$CH$_3$ (SEQ ID NO:2)

In the reaction vessel of a Rainin peptide synthesizer Fmoc-Pro-Sieber ethylamide resin (0.25 g, 0.4 mmol/g loading) was placed. The resin was solvated with DMF and amino acids were coupled sequentially according to the following synthetic cycle:
(1) 3×1.5 minute washes with DMF;
(2) 2×15 minute deprotections using 20% piperidine;
(3) 6×3 minute washes with DMF;
(4) addition of amino acid;
(5) activation of amino acid with 0.4 M HBTU/NMM and coupling;
(6) 3×1.5 minute washes with DMF.

The protected amino acids were coupled to the resin in the following order:

| Protected Amino Acid | Coupling time |
| --- | --- |
| Fmoc-Arg(Pmc) | 30 minutes |
| Fmoc-Ile | 30 minutes |
| Fmoc-Nva | 30 minutes |
| acetic acid | 30 minutes |

Upon completion of the synthesis the peptide was cleaved from the resin using a mixture of (95:2.5:2.5) TFA/anisole/water for 3 hours. The peptide solution was concentrated under vacuum and precipitated with diethyl ether. The crude peptide was collected by filtration and purified by HPLC using a C-18 column and a solvent mixture varying over 50 minutes from 5% to 100% acetonitrile/water containing 0.01% TFA. The pure fractions were lyophilized to provide N-Ac-Nva-Ile-Arg-Pro-NHCH$_2$CH$_3$ as the trifluoroacetate salt: Rt=1.28 minutes (gradient varying over 10 minutes from 20% to 80% acetonitrile/water containing 0.01% TFA); MS (ESI) m/e 553 (M+H)$^+$; Amino Acid Anal.: 0.99 Nva; 1.01 Ile; 1.03 Arg; 1.00 Pro.

EXAMPLE 2

N-Ac-Gln-Ile-Arg-Pro-NHCH$_2$CH$_3$ (SEQ ID NO:3)

The desired product was prepared by substituting Fmoc-Gln(Trt) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Gln-Ile-Arg-Pro-NHCH$_2$CH$_3$ as the trifluoroacetate salt: Rt=3.40 minutes (gradient varying over 10 minutes from 20% to 80% acetonitrile/water containing 0.01% TFA); MS (ESI) m/e 553 (M+H)$^+$; Amino Acid Anal.: 1.04 Glu; 1.00 Ile; 1.02 Arg; 0.98 Pro.

EXAMPLE 3

N-(6-methylnicotinyl)-Nva-Ile-Arg-Pro-NHCH$_2$CH$_3$ (SEQ ID NO:4)

The desired product was prepared by substituting 6-methylnicotinic acid for acetic acid. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-(6-methylnicotinyl)-Nva-Ile-Arg-Pro-NHCH$_2$CH$_3$ as the trifluoroacetate salt: Rt=4.01 minutes (gradient varying over 10 minutes from 20% to 80% acetonitrile/water containing 0.01% TFA); MS (ESI) m/e 630.4 (M+H)$^+$; Amino Acid Anal.: 1.02 Nva; 1.01 Ile; 1.05 Arg; 1.03 Pro.

EXAMPLE 4

N-Ac-Ser-Ile-Arg-Pro-NHCH$_2$CH$_3$ (SEQ ID NO:5)

The desired product was prepared by substituting Fmoc-Ser(t-Bu) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Ser-Ile-Arg-Pro-NHCH$_2$CH$_3$ as the trifluoroacetate salt: Rt=3.011 minutes (gradient varying over 10 minutes from 20% to 80% acetonitrile/water containing 0.01% TFA); MS (ESI) m/e 541.2 (M+H)$^+$.

EXAMPLE 5

N-Ac-Nva-D-Ile-Arg-Pro-NHCH$_2$CH$_3$

The desired product was prepared by substituting Fmoc-D-Ile for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Nva-D-Ile-Arg-Pro-NHCH$_2$CH$_3$ as the trifluoroacetate salt: Rt=4.508 minutes (gradient varying over 10 minutes from 20% to 80% acetonitrile/water containing 0.01% TFA); MS (ESI) m/e 553.2 (M+H)$^+$.

EXAMPLE 6

N-Ac-Nle-Ile-Arg-Pro-NHCH$_2$CH$_3$ (SEQ ID NO:6)

The desired product was prepared by substituting Fmoc-Nle for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Nle-Ile-Arg-Pro-NHCH$_2$CH$_3$ as the trifluoroacetate salt: Rt=4.547 minutes (gradient varying over 10 minutes from 20% to 80% acetonitrile/water containing 0.01% TFA); MS (ESI) m/e 567.3 (M+H)$^+$.

EXAMPLE 7

N-Ac-D-Nva-Ile-Arg-Pro-NHCH$_2$CH$_3$

The desired product was prepared by substituting Fmoc-D-Nva for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Nva-Ile-Arg-Pro-NHCH$_2$CH$_3$ as the trifluoroacetate salt: Rt=4.43 minutes (gradient varying over 10 minutes from 20% to 80% acetonitrile/water containing 0.01% TFA); MS (ESI) m/e 553.2 (M+H)$^+$.

EXAMPLE 8

N-Ac-Gln-Ile-Arg-Pro-D-AlaNH$_2$

The desired product was prepared by substituting Fmoc-Gln(Trt) for Fmoc-Nva and Fmoc-D-Ala-Sieber amide resin for Fmoc-Pro-Sieber ethylamide resin and adding a coupling with Fmoc-Pro before the coupling with Fmoc-Arg(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Gln-Ile-Arg-Pro-D-AlaNH$_2$ as the trifluoroacetate salt: Rt=3.054 minutes (gradient varying over 10 minutes from 20% to 80% acetonitrile/water containing 0.01% TFA); MS (ESI) m/e 625.3 (M+H)$^+$.

EXAMPLE 9

N-Ac-Nva-Ile-Arg-Pro-D-AlaNH$_2$

The desired product was prepared by substituting Fmoc-D-Ala-Sieber amide resin for Fmoc-Pro-Sieber ethylamide resin and adding a coupling with Fmoc-Pro before the coupling with Fmoc-Arg-(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Nva-Ile-Arg-Pro-D-AlaNH$_2$ as the trifluoroacetate salt: Rt=3.826 minutes (gradient varying over 10 minutes from 20% to 80% acetonitrile/water containing 0.01% TFA); MS (ESI) m/e 596.3 (M+H)$^+$.

EXAMPLE 10

N-Ac-Leu-Ile-Arg-Pro-NHCH$_2$CH$_3$ (SEQ ID NO:7)

The desired product was prepared by substituting Fmoc-Leu for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Leu-Ile-Arg-Pro-NHCH$_2$CH$_3$ as the trifluoroacetate salt: Rt=4.469 minutes (gradient varying over 10 minutes from 20% to 80% acetonitrile/water containing 0.01% TFA); MS (ESI) m/e 567.2 (M+H)$^+$.

EXAMPLE 11

N-Ac-Lys(Ac)-Ile-Arg-Pro-NHCH$_2$CH$_3$ (SEQ ID NO:8)

The desired product was prepared by substituting Fmoc-Lys(Ac) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Lys(Ac)-Ile-Arg-Pro-NHCH$_2$CH$_3$ as the trifluoroacetate salt: Rt=3.678 minutes (gradient varying over 10 minutes from 20% to 80% acetonitrile/water containing 0.01% TFA); MS (ESI) m/e 624.3 (M+H)$^+$.

EXAMPLE 12

N-Ac-Gly-Ile-Arg-Pro-NHCH$_2$CH$_3$ (SEQ ID NO:9)

The desired product was prepared by substituting Fmoc-Gly for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Gly-Ile-Arg-Pro-NHCH$_2$CH$_3$ as the trifluoroacetate salt: Rt=3.249 minutes (gradient varying over 10 minutes from 20% to 80% acetonitrile/water containing 0.01% TFA); MS (ESI) m/e 511.2 (M+H)$^+$.

EXAMPLE 13

N-Ac-alloThr-Ile-Arg-Pro-NHCH$_2$CH$_3$ (SEQ ID NO: 10)

The desired product was prepared by substituting Fmoc-alloThr(t-Bu) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-allo-Thr-Ile-Arg-Pro-NHCH$_2$CH$_3$ as the trifluoroacetate salt: Rt=3.363 minutes (gradient varying over 10 minutes from 20% to 80% acetonitrile/water containing 0.01% TFA); MS (ESI) m/e 555.2 (M+H)$^+$; Amino Acid Anal.: 0.56 Thr; 0.96 Ile; 0.99 Arg; 1.12 Pro.

EXAMPLE 14

N-Ac-alloThr-D-Ile-Arg-Pro-NHCH$_2$CH$_3$

The desired product was prepared by substituting Fmoc-alloThr(t-Bu) for Fmoc-Nva and Fmo-D-Ile for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-alloThr-D-Ile-Arg-Pro-NHCH$_2$CH$_3$ as the trifluoroacetate salt: Rt=3.319 minutes (gradient varying over 10 minutes from 20% to 80% acetonitrile/water containing 0.01% TFA); MS (ESI) m/e 555.2 (M+H)$^+$.

EXAMPLE 15

N-Ac-Trp-Ile-Arg-Pro-NHCH$_2$CH$_3$ (SEQ ID NO: 11)

The desired product was prepared by substituting Fmoc-Trp(Boc) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Trp-Ile-Arg-Pro-NHCH$_2$CH$_3$ as the trifluoroacetate salt: Rt=5.063 minutes (gradient varying over 10 minutes from 20% to 80% acetonitrile/water containing 0.01% TFA); MS (ESI) m/e 640.3 (M+H)$^+$.

EXAMPLE 16

N-Ac-Trp-Ile-Arg-Pro-D-AlaNH$_2$

The desired product was prepared by substituting Fmoc-Trp(Boc) for Fmoc-Nva and Fmoc-D-Ala-Sieber amide resin for Fmoc-Pro-Sieber ethylamide resin and adding a coupling with Fmoc-Pro before the coupling with Fmoc-Arg(Pmc) in Example 1. After workup the crude peptide was purified by HPLC using C-18 column and with a solvent mixture varying over 50 minutes in a gradient from 5% to 100% acetonitrile-water containing 0.01% TFA. The pure fractions were lyophilized to give N-Ac-Trp-Ile-Arg-Pro-D-AlaNH$_2$ as trifluoroacetate salt: Rt=4.739 minutes (gradient varying over 10 minutes from 20% to 80% acetonitrile/water containing 0.01% TFA); MS (ESI) m/e 683.3 (M+H)$^+$; Amino Acid Anal.: 0.4 Trp; 1.0 Ile; 0.99 Arg; 1.063 Pro; 1.064 Ala.

EXAMPLE 18

N-Ac-Thr-Ile-Arg-Pro-D-AlaNH$_2$

The desired product was prepared by substituting Fmoc-Thr(t-Bu) for Fmoc-Nva and Fmoc-D-Ala-Sieber amide resin for Fmoc-Pro-Sieber ethylamide resin and adding a coupling with Fmoc-Pro before the coupling with Fmoc-Arg(Pmc) in Example 1. After workup the crude peptide was purified by HPLC using C-18 column and with a solvent mixture varying over 50 minutes in a gradient from 5% to 100% acetonitrile-water containing 0.01% TFA. The pure fractions were lyophilized to give N-Ac-Thr-Ile-Arg-Pro-D-AlaNH$_2$ as trifluoroacetate salt: Rt=3.042 minutes (gradient varying over 10 minutes from 20% to 80% acetonitrile/water containing 0.01% TFA); MS (ESI) m/e 598.2 (M+H)$^+$; Amino Acid Anal.: 0.42 Thr; 1.04 Ile; 0.83 Arg; 1.06 Pro; 1.07 Ala.

EXAMPLE 19

N-Ac-Thr-D-Ile-Arg-Pro-D-AlaNH$_2$

The desired product was prepared by substituting Fmoc-Thr(t-Bu) for Fmoc-Nva, Fmoc-D-Ile for Fmoc-Ile, and Fmoc-D-Ala-Sieber amide resin for Fmoc-Pro-Sieber ethylamide resin and adding a coupling with Fmoc-Pro before the coupling with Fmoc-Arg(Pmc) in Example 1. After workup the crude peptide was purified by HPLC using C-18 column and with a solvent mixture varying over 50 minutes in a gradient from 5% to 100% acetonitrile-water containing 0.01% TFA. The pure fractions were lyophilized to give N-Ac-Thr-D-Ile-Arg-Pro-D-AlaNH$_2$ as trifluoroacetate salt: Rt=3.271 minutes (gradient varying over 10 minutes from 20% to 80% acetonitrile/water containing 0.01% TFA); MS (ESI) m/e 598.2 (M+H)$^+$; Amino Acid Anal.: 0.419 Thr; 1.08 Ile; 0.98 Arg; 1.01 Pro; 1.094 Ala.

EXAMPLE 20

N-Ac-Ser-Ile-Arg-Pro-D-AlaNH$_2$

The desired product was prepared by substituting Fmoc-Ser(t-Bu) for Fmoc-Nva, Fmoc-D-Ala-Sieber amide resin for Fmoc-Pro-Sieber ethylamide resin, and adding a coupling with Fmoc-Pro before the coupling with Fmoc-Arg(Pmc) in Example 1. After workup the crude peptide was purified by HPLC using C-18 column and with a solvent mixture varying over 50 minutes in a gradient from 5% to 100% acetonitrile-water containing 0.01% TFA. The pure fractions were lyophilized to give N-Ac-Ser-Ile-Arg-Pro-D-AlaNH$_2$ as trifluoroacetate salt: Rt=2.983 minutes (gradient varying over 10 minutes from 20% to 80% acetonitrile/water containing 0.01% TFA); MS (ESI) m/e 584.2 (M+H)$^+$.

EXAMPLE 21

N-Ac-Thr-Pro-Arg-Pro-NHCH$_2$CH$_3$ (SEQ ID NO:12)

The procedure described in Example 1 was used but substituting Fmoc-Thr(t-Bu) for Fmoc-Nva and Fmoc-Pro for Fmoc-Ile. After workup the crude peptide was purified by HPLC using C-18 column and with a solvent mixture varying over 50 minutes in a gradient from 5% to 100% acetonitrile-water containing 0.01% TFA. The pure fractions were lyophilized to give N-Ac-Thr-Pro-Arg-Pro-NHCH$_2$CH$_3$ as trifluoroacetate salt: Rt=2.68 minutes (gradient varying over 10 minutes from 20% to 80% acetonitrile/water containing 0.01% TFA); MS (ESI) m/e 555.2 (M+H)$^+$; Amino Acid Anal.: 0.40 Thr; 0.91 Arg; 2.03 Pro.

EXAMPLE 22

N-Ac-allylGly-Ile-Arg-Pro-NHCH$_2$CH$_3$ (SEQ ID NO:13)

The procedure described in Example 1 was used but substituting Fmoc-Allygly for Fmoc-Nva. After workup the crude peptide was purified by HPLC using C-18 column and with a solvent mixture varying over 50 minutes in a gradient from 5% to 100% acetonitrile-water containing 0.01% TFA. The pure fractions were lyophilized to give N-Ac-Allylgly-Ile-Arg-Pro-NHCH$_2$CH$_3$ as trifluoroacetate salt: Rt=3.721 minutes (gradient varying over 10 minutes from 20% to 80% acetonitrile/water containing 0.01% TFA); MS (ESI) m/e 551.2 (M+H)$^+$; Amino Acid Anal.: 1.0 Ile; 0.97 Arg; 1.03 Pro.

Example 23

N-Ac-Gln-Ile-Arg-NHCH$_2$CH$_3$

The procedure described in Example 1 was used but substituting Fmoc-Arg(Pbf)-[4-(4-N-ethyl)methyl-3-methoxyphenoxy]butyryl AM resin for Fmoc-Pro Sieber ethylamide resin, Fmoc-Gln(Trt) for Fmoc-Nva, and omitting the coupling with Fmoc-Arg(Pmc). After cleavage of the peptide from the resin and workup the crude product was purified by HPLC using C-18 column and a solvent mixture varying over 50 minutes in a gradient from 5% to 100% acetonitrile-water containing 0.01% TFA. The pure fractions were lyophilized to give N-Ac-Gln-Ile-Arg-NHCH$_2$CH$_3$ as the trifluoroacetate salt: Rt=0.65 minutes (gradient varying over 10 minutes from 20% to 80% acetonitrile/water containing 0.01% TFA); MS (ESI) m/e 485.2 (M+H)$^+$.

EXAMPLE 24

N-Ac-D-Trp-Ile-Arg-Pro-NHCH$_2$CH$_3$

The procedure described in Example 1 can be used by substituting Fmoc-D-Trp(Boc) for Fmoc-Nva. After workup the crude peptide can be purified by HPLC using C-18 column and with a solvent mixture varying over 50 minutes in a gradient from 5% to 100% acetonitrile-water containing 0.01% TFA. The pure fractions can be lyophilized to give N-Ac-D-Trp-Ile-Arg-Pro-NH CH$_2$CH$_3$ as trifluoroacetate salt.

EXAMPLE 25

N-Ac-Arg-Ile-Arg-Pro-NHCH$_2$CH$_3$ (SEQ ID NO: 14)

The procedure described in Example 1 can be used by substituting Fmoc-Arg(Pmc) for Fmoc-Nva. After workup the crude peptide can be purified by HPLC using C-18 column and with a solvent mixture varying over 50 minutes in a gradient from 5% to 100% acetonitrile-water containing 0.01% TFA. The pure fractions can be lyophilized to give N-Ac-Arg-Ile-Arg-Pro-NH CH$_2$CH$_3$ as trifluoroacetate salt.

EXAMPLE 26

N-Ac-Ser-Cit-Arg-Pro-NHCH$_2$CH$_3$ (SEQ ID NO: 15)

The procedure described in Example 1 can be used by substituting Fmoc-Ser(t-Bu) for Fmoc-Nva and Fmoc-Cit for Fmoc-Ile. After workup the crude peptide can be purified by HPLC using C-18 column and with a solvent mixture varying over 50 minutes in a gradient from 5% to 100% acetonitrile-water containing 0.01% TFA. The pure fractions can be lyophilized to give N-Ac-Ser-Cit-Arg-Pro-NHCH$_2$CH$_3$ as trifluoroacetate salt.

EXAMPLE 27

N-Ac-Nva-Lys(Ac)-Arg-Pro-NHCH$_2$CH$_3$ (SEQ ID NO:16)

The procedure described in Example 1 can be used by substituting Fmoc-Lys(Ac) for Fmoc-Ile. After workup the crude peptide can be purified by HPLC using C-18 column and with a solvent mixture varying over 50 minutes in a gradient from 5% to 100% acetonitrile-water containing 0.01% TFA. The pure fractions can be lyophilized to give N-Ac-Nva-Lys(Ac)-Arg-Pro-NHCH$_2$CH$_3$ as trifluoroacetate salt.

EXAMPLE 28

N-Ac-D-Gln-Ile-Arg-Pro-D-AlaNH$_2$

The procedure described in Example 1 can be used but substituting Fmoc-D-Gln(Trt) for Fmoc-Nva, Fmoc-D-Ala-Sieber amide resin for Fmoc-Pro-Sieber ethylamide resin and coupling with Fmoc-Pro before coupling with Fmoc-Arg(Pmc). After workup the crude peptide can be purified by HPLC using C-18 column and with a solvent mixture varying over 50 minutes in a gradient from 5% to 100% acetonitrile-water containing 0.01% TFA. The pure fractions can be lyophilized to give N-Ac-D-Gln-Ile-Arg-Pro-D-AlaNH$_2$ as trifluoroacetate salt.

EXAMPLE 29

N-Ac-bAla-Nva-Ile-Arg-Pro-NHCH$_2$CH$_3$ (SEQ ID NO: 17)

The procedure described in Example 1 can be used by substituting N-Ac-bAla for acetic acid. After workup the crude peptide can be purified by HPLC using C-18 column and with a solvent mixture varying over 50 minutes in a gradient from 5% to 100% acetonitrile-water containing 0.01% TFA. The pure fractions can be lyophilized to give N-Ac-bAla-Nva-Ile-Arg-Pro-NHCH$_2$CH$_3$ as trifluoroacetate salt.

EXAMPLE 30

N-Ac-Nva-Ile-Arg-NHCH$_2$CH$_3$

The procedure described in Example 1 can be used but substituting Fmoc-Arg(Pbf)-[4-(4-N-ethyl)methyl-3-methoxyphenoxy]butyryl AM resin for Fmoc-Pro Sieber ethylamide resin and omitting the coupling with Fmoc-Arg(Pmc). After cleavage of the peptide from the resin and workup the crude product can be purified by HPLC using C-18 column and with a solvent mixture varying over 50 minutes in a gradient from 5% to 100% acetonitrile-water containing 0.01% TFA. The pure fractions can be lyophilized to give N-Ac-Nva-Ile-Arg-NHCH$_2$CH$_3$ as the trifluoroacetate salt.

EXAMPLE 31

N-Ac-Nva-Ile-Arg-Pro-NHCH(CH$_3$)$_2$ (SEQ ID NO: 18)

The procedure described in Example 1 can be used but substituting Fmoc-Pro-[4-(4-N-isopropylamino)methyl-3-methoxyphenoxy]butyryl AM resin for Fmoc-Pro Sieber ethylamide resin. After cleavage of the peptide from the resin and workup the crude product can be purified by HPLC using C-18 column and with a solvent mixture varying over 50 minutes in a gradient from 5% to 100% acetonitrile-water containing 0.01% TFA. The pure fractions can be lyophilized to give N-Ac-Nva-Ile-Arg-Pro-NHCH(CH$_3$)$_2$ as the trifluoroacetate salt.

EXAMPLE 32

N-Ac-Gln-Ile-Arg-Pro-NH CH$_3$)$_2$ (SEQ ID NO: 19)

The procedure described in Example 1 can be used but substituting Fmoc-Pro-[4-(4-N-isopropylamino)methyl-3-methoxyphenoxy]butyryl AM resin for Fmoc-Pro Sieber ethylamide resin and Fmoc-Gln(Trt) for Fmoc-Nva. After cleavage of the peptide from the resin and workup the crude product can be purified by HPLC using C-18 column and with a solvent mixture varying over 50 minutes in a gradient from 5% to 100% acetonitrile-water containing 0.01% TFA. The pure fractions can be lyophilized to give N-Ac-Gln-Ile-Arg-Pro-NHCH(CH$_3$)$_2$ as the trifluoroacetate salt.

EXAMPLE 33

N-Ac-D-Gln-Ile-Arg-Pro-NHCH$_2$CH$_3$

The procedure described in Example 1 can be used by substituting Fmoc-D-Gln(Trt) for Fmoc-Nva. After workup the crude peptide can be purified by HPLC using C-18 column and with a solvent mixture varying over 50 minutes in a gradient from 5% to 100% acetonitrile-water containing 0.01% TFA. The pure fractions can be lyophilized to give N-Ac-D-Gln-Ile-Arg-Pro-NHCH$_2$CH$_3$ as trifluoroacetate salt.

EXAMPLE 34

N-Ac-D-Nva-Ile-Arg-NHCH$_2$CH$_3$

The procedure described in Example 1 can be used but substituting Fmoc-Arg(Pbf)-[4-(4-N-ethyl)methyl-3-methoxyphenoxy]butyryl AM resin for Fmoc-Pro Sieber ethylamide resin, Fmoc-D-Nva for Fmoc-Nva, and omitting the coupling with Fmoc-Arg(Pmc). After cleavage of the peptide from the resin and workup the crude product can be purified by HPLC using C-18 column and with a solvent mixture varying over 50 minutes in a gradient from 5% to 100% acetonitrile-water containing 0.01% TFA. The pure fractions can be lyophilized to give N-Ac-D-Nva-Ile-Arg-NHCH$_2$CH$_3$ as the trifluoroacetate salt.

EXAMPLE 35

N-Ac-Lys(Ac)-Ile-Arg-NHCH$_2$CH$_3$

The procedure described in Example 1 can be used but substituting Fmoc-Arg(Pbf)-[4-(4-N-ethyl)methyl-3-methoxyphenoxy]butyryl AM resin for Fmoc-Pro Sieber ethylamide resin, Fmoc-Lys(Ac) for Fmoc-Nva, and omitting the coupling with Fmoc-Arg(Pmc). After cleavage of the peptide from the resin and workup the crude product can be purified by HPLC using C-18 column and with a solvent mixture varying over 50 minutes in a gradient from 5% to 100% acetonitrile-water containing 0.01% TFA. The pure fractions can be lyophilized to give N-Ac-Lys(Ac)-Ile-Arg-NHCH$_2$CH$_3$ as the trifluoroacetate salt.

EXAMPLE 36

N-Ac-Thr-Ile-Arg-NHCH$_2$CH$_3$

The procedure described in Example 1 can be used but substituting Fmoc-Arg(Pbf)-[4-(4-N-ethyl)methyl-3-methoxyphenoxy]butyryl AM resin for Fmoc-Pro Sieber ethylamide resin, Fmoc-Thr(t-Bu) for Fmoc-Nva and omitting the coupling with Fmoc-Arg(Pmc). After cleavage of the peptide from the resin and workup the crude product can be purified by HPLC using C-18 column and with a solvent mixture varying over 50 minutes in a gradient from 5% to 100% acetonitrile-water containing 0.01% TFA. The pure fractions can be lyophilized to give N-Ac-Thr-Ile-Arg-NHCH$_2$CH$_3$ as the trifluoroacetate salt.

EXAMPLE 37

N-Ac-Nva-Lys(Ac)-Arg-NHCH$_2$CH$_3$

The procedure described in Example 1 can be used but substituting Fmoc-Arg(Pbf)-[4-(4-N-ethyl)methyl-3-methoxyphenoxy]butyryl AM resin for Fmoc-Pro Sieber ethylamide resin, Fmoc-Lys(Ac) for Fmoc-Ile, and omitting the coupling with Fmoc-Arg(Pmc). After cleavage of the peptide from the resin and workup the crude product can be purified by HPLC using C-18 column and with a solvent mixture varying over 50 minutes in a gradient from 5% to 100% acetonitrile-water containing 0.01% TFA. The pure fractions can be lyophilized to give N-Ac-Nva-Lys(Ac)-Arg-NHCH$_2$CH$_3$ as the trifluoroacetate salt.

EXAMPLE 38

N-Ac-Trp-Pro-Arg-NHCH$_2$CH$_3$

The procedure described in Example 1 can be used but substituting Fmoc-Arg(Pbf)-[4-(4-N-ethyl)methyl-3-methoxyphenoxy]butyryl AM resin for Fmoc-Pro Sieber ethylamide resin, Fmoc-Pro for Fmoc-Ile, Fmoc-Trp(Boc) for Fmoc-Nva, and omitting the coupling with Fmoc-Arg(Pmc). After cleavage of the peptide from the resin and workup the crude product can be purified by HPLC using C-18 column and with a solvent mixture varying over 50 minutes in a gradient from 5% to 100% acetonitrile-water containing 0.01% TFA. The pure fractions can be lyophilized to give N-Ac-Trp-Pro-Arg-NHCH$_2$CH$_3$ as the trifluoroacetate salt.

EXAMPLE 39

N-Ac-D-Ser-Ile-Arg-NHCH$_2$CH$_3$

The procedure described in Example 1 can be used but substituting Fmoc-Arg(Pbf)-[4-(4-N-ethyl)methyl-3-methoxyphenoxy]butyryl AM resin for Fmoc-Pro Sieber ethylamide resin, Fmoc-D-Ser(t-Bu) for Fmoc-Nva, and omitting the coupling with Fmoc-Arg(Pmc). After cleavage of the peptide from the resin and workup the crude product can be purified by HPLC using C-18 column and with a solvent mixture varying over 50 minutes in a gradient from 5% to 100% acetonitrile-water containing 0.01% TFA. The pure fractions can be lyophilized to give N-Ac-DSer-Ile-Arg-NHCH$_2$CH$_3$ as the trifluoroacetate salt.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

SEQUENCE LISTING

```
<160> NUMBER OF SEQ ID NOS: 19

<210> SEQ ID NO 1
<211> LENGTH: 6
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = hydrogen or R-(CH2)n-C-(O)-, wherein n is
      an integer from 0 to 8, R is alkoxy, alkyl, amino, aryl, carboxyl,
      cycloalkenyl, cycloalkyl, and heterocycle at position 1
<220> FEATURE:
<221> NAME/KEY: VARIANT
<222> LOCATION: (2)...(2)
<223> OTHER INFORMATION: Xaa = N-methylalanyl, alloThr, allylGly, Arg,
      bAla, Gln, Gly, Hser, Leu, Lys(Ac), Nle, Nva,
      NMeNva, and Orn(Ac) at position 2
<220> FEATURE:
<221> NAME/KEY: VARIANT
<222> LOCATION: (2)...(2)
<223> OTHER INFORMATION: 2 (Continued)
      Xaa = 3-Pal, Sar, Ser, N-methylseryl, Thr, Trp,
      Val, and N-methylvalyl at position 2
<220> FEATURE:
<221> NAME/KEY: VARIANT
<222> LOCATION: (3)...(3)
<223> OTHER INFORMATION: Xaa = Ala, aIle, Asp, Cit, Ile,
      N-methylisoleucyl, Leu, Lys(Ac), Nva, Phe, and Pro at position 3
<220> FEATURE:
<221> NAME/KEY: VARIANT
<222> LOCATION: (4)...(4)
<223> OTHER INFORMATION: Xaa = Arg, Cit, His, Ile, Lys, lysyl(N-epsilon
      isopropyl), Orn, and 3-Pal at position 4
<220> FEATURE:
<221> NAME/KEY: VARIANT
<222> LOCATION: (5)...(5)
<223> OTHER INFORMATION: Xaa = 2-aminobutyryl, 2-aminoisobutyryl, Arg,
      homoprolyl, hydroxyprolyl, Leu, Phe, and Pro  at
      position 5
```

```
<220> FEATURE:
<221> NAME/KEY: VARIANT
<222> LOCATION: (6)...(6)
<223> OTHER INFORMATION: Xaa = hydroxyl, azaglycylamide, glycylamide,
      prolylethylamide, NHCH(CH3)2, -NH-(CH2)n-CHR1R2,
      -NHR3, wherein n is an integer from 0 to 8 at
      position 6
<220> FEATURE:
<221> NAME/KEY: VARIANT
<222> LOCATION: (6)...(6)
<223> OTHER INFORMATION: 6 (Continued)
      Xaa = R1 is hydrogen, alkyl, cycloalkenyl, and
      cycloalkyl at position 6
<220> FEATURE:
<221> NAME/KEY: VARIANT
<222> LOCATION: (6)...(6)
<223> OTHER INFORMATION: 6 (Continued)
      Xaa = R2 is hydrogen, alkoxy, alkyl, aryl,
      cycloalkenyl, cycloalkyl, heterocycle, and
      hydroxyl at position 6
<220> FEATURE:
<221> NAME/KEY: VARIANT
<222> LOCATION: (6)...(6)
<223> OTHER INFORMATION: 6 (Continued)
      Xaa = with the proviso that when n is 0, R2 is
      other than alkoxy or hydroxyl at position 6
<220> FEATURE:
<221> NAME/KEY: VARIANT
<222> LOCATION: (6)...(6)
<223> OTHER INFORMATION: 6 (Continued)
      Xaa = R3 is hydrogen, cycloalkenyl, cycloalkyl,
      and hydroxyl at position 6

<400> SEQUENCE: 1

Xaa Xaa Xaa Xaa Xaa Xaa
 1               5

<210> SEQ ID NO 2
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = Nva at position 1
<220> FEATURE:
<221> NAME/KEY: VARIANT
<222> LOCATION: (4)...(4)
<223> OTHER INFORMATION: Xaa = prolylethylamide at position 4

<400> SEQUENCE: 2

Xaa Ile Arg Xaa
 1

<210> SEQ ID NO 3
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = prolylethylamide at position 4

<400> SEQUENCE: 3

Gln Ile Arg Xaa
 1
```

```
<210> SEQ ID NO 4
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = N-(6-methylnicotinyl) at position 1
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 4

Xaa Xaa Ile Arg Xaa
 1               5

<210> SEQ ID NO 5
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = prolylethylamide at position 4

<400> SEQUENCE: 5

Ser Ile Arg Xaa
 1

<210> SEQ ID NO 6
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = Nle at position 1
<220> FEATURE:
<221> NAME/KEY: VARIANT
<222> LOCATION: (4)...(4)
<223> OTHER INFORMATION: Xaa = prolylethylamide at position 4

<400> SEQUENCE: 6

Xaa Ile Arg Xaa
 1

<210> SEQ ID NO 7
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = prolylethylamide at position 4
```

```
<400> SEQUENCE: 7

Leu Ile Arg Xaa
 1

<210> SEQ ID NO 8
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = Lys(Ac) at position 1
<220> FEATURE:
<221> NAME/KEY: VARIANT
<222> LOCATION: (4)...(4)
<223> OTHER INFORMATION: Xaa = prolylethylamide at position 4

<400> SEQUENCE: 8

Xaa Ile Arg Xaa
 1

<210> SEQ ID NO 9
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = prolylethylamide at position 4

<400> SEQUENCE: 9

Gly Ile Arg Xaa
 1

<210> SEQ ID NO 10
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = alloThr at position 1
<220> FEATURE:
<221> NAME/KEY: VARIANT
<222> LOCATION: (4)...(4)
<223> OTHER INFORMATION: Xaa = prolylethylamide at position 4

<400> SEQUENCE: 10

Xaa Ile Arg Xaa
 1

<210> SEQ ID NO 11
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = prolylethylamide at position 4
```

```
<400> SEQUENCE: 11

Trp Ile Arg Xaa
1

<210> SEQ ID NO 12
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = prolylethylamide at position 4

<400> SEQUENCE: 12

Thr Pro Arg Xaa
1

<210> SEQ ID NO 13
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = allylGly at position 1
<220> FEATURE:
<221> NAME/KEY: VARIANT
<222> LOCATION: (4)...(4)
<223> OTHER INFORMATION: Xaa = prolylethylamide at position 4

<400> SEQUENCE: 13

Xaa Ile Arg Xaa
1

<210> SEQ ID NO 14
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = prolylethylamide at position 4

<400> SEQUENCE: 14

Arg Ile Arg Xaa
1

<210> SEQ ID NO 15
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Cit at position 2
<220> FEATURE:
<221> NAME/KEY: VARIANT
<222> LOCATION: (4)...(4)
<223> OTHER INFORMATION: Xaa = prolylethylamide at position 4
```

-continued

```
<400> SEQUENCE: 15

Ser Xaa Arg Xaa
 1

<210> SEQ ID NO 16
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = Nva at position 1
<220> FEATURE:
<221> NAME/KEY: VARIANT
<222> LOCATION: (2)...(2)
<223> OTHER INFORMATION: Xaa = Lys(Ac) at position 2
<220> FEATURE:
<221> NAME/KEY: VARIANT
<222> LOCATION: (4)...(4)
<223> OTHER INFORMATION: Xaa = prolylethylamide at position 4

<400> SEQUENCE: 16

Xaa Xaa Arg Xaa
 1

<210> SEQ ID NO 17
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = bAla at position 1
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 17

Xaa Xaa Ile Arg Xaa
 1               5

<210> SEQ ID NO 18
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = Nva at position 1
<220> FEATURE:
<221> NAME/KEY: VARIANT
<222> LOCATION: (4)...(4)
<223> OTHER INFORMATION: Xaa = prolylisopropylamide at position 4

<400> SEQUENCE: 18

Xaa Ile Arg Xaa
 1
```

```
<210> SEQ ID NO 19
<211> LENGTH: 4
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = prolylisopropylamide at position 4

<400> SEQUENCE: 19

Gln Ile Arg Xaa
 1
```

What is claimed is:

1. A compound of formula (I)

$$Xaa_1\text{-}Xaa_2\text{-}Xaa_3\text{-}Xaa_4\text{-}Xaa_5\text{-}Xaa_6 \text{ (SEQ ID NO: 1)} \quad (I),$$

or a therapeutically acceptable salt thereof, wherein $Xaa_1$ is R—$(CH_2)_n$—C(O)—, wherein n is an integer from 0 to 8 and R is selected from the group consisting of alkoxy, alkyl, amino, aryl, carboxyl, cycloalkenyl, cycloalkyl, and heterocycle;

$Xaa_2$ is selected from the group consisting of N-methylalanyl, allothreonyl, allylglycyl, arginyl, beta-alanyl, glutaminyl, D-glutaminyl, glycyl, homoseryl, leucyl, lysyl(N-epsilon acetyl), norleucyl, norvalyl, D-norvalyl, N-methylnorvalyl, ornithyl(N-delta acetyl), 3-(3-pyridyl)alanyl, sarcosyl, seryl, D-seryl, N-methylseryl, threonyl, tryptyl, D-tryptyl, valyl, and N-methylvalyl;

$Xaa_3$ is selected from the group consisting of alanyl, alloisoleucyl, aspartyl, citrullyl, isoleucyl, D-isoleucyl, N-methylisoleucyl, leucyl, D-leucyl, lysyl(N-epsilon acetyl), D-lysyl(N-epsilon acetyl), norvalyl, phenylalanyl, prolyl, and D-prolyl;

$Xaa_4$ is selected from the group consisting of arginyl, D-arginyl, citrullyl, histidyl, isoleucyl, lysyl, lysyl(N-epsilon isopropyl), ornithyl, and 3-(3-pyridyl)alanyl;

$Xaa_5$ is absent or selected from the group consisting of N-methyl-D-alanyl, 2-aminobutyryl, 2-aminoisobutyryl, arginyl, D-glutaminyl, homoprolyl, hydroxyprolyl, leucyl, phenylalanyl, prolyl, D-prolyl, and D-valyl; provided that when $Xaa_4$ is arginyl or D-arginyl then $Xaa_5$ is other than arginyl; and $Xaa_6$ is selected from the group consisting of hydroxyl, D-alanylamide, azaglycylamide, glycylamide, D-lysyl (N-epsilon acetyl)amide, prolylethylamide, —NHCH $(CH_3)_2$, a group represented by the formula —NH— $(CH_2)_n$—$CHR^1R^2$, and a group represented by the formula —$NHR^3$, wherein n is an integer from 0 to 8; $R^1$ is selected from the group consisting of hydrogen, alkyl, cycloalkenyl, and cycloalkyl; $R^2$ is selected from the group consisting of hydrogen, alkoxy, alkyl, aryl, cycloalkenyl, cycloalkyl, heterocycle, and hydroxyl, with the proviso that when n is 0, $R^2$ is other than alkoxy or hydroxyl; and $R^3$ is selected from the group consisting of hydrogen, cycloalkenyl, cycloalkyl, and hydroxyl.

2. The compound of claim 1 wherein
$Xaa_1$ is R—$(CH_2)_n$—C(O)—;
n is 0;

R is selected from the group consisting of alkyl and heterocycle, wherein the alkyl is methyl, and wherein the heterocycle is 6-methylpyridinyl;

$Xaa_2$ is selected from the group consisting of allylglycyl, arginyl, beta-alanyl, norleucyl, leucyl, lysyl(N-epsilon-acetyl), glycyl, glutaminyl, D-glutaminyl, norvalyl, D-norvalyl, seryl, D-seryl, allothreonyl, threonyl, tryptyl, and D-tryptyl;

$Xaa_3$ is selected from the group consisting of citrullyl, isoleucyl, D-isoleucycl, lysyl(N-epsilon-acetyl), norvalyl, and prolyl;

$Xaa_4$ is selected from the group consisting of arginyl and isoleucyl;

$Xaa_5$ is absent or selected from the group consisting of prolyl and arginyl; and $Xaa_6$ is selected from the group consisting of —$NHCH_2CH_3$, —$NHCH(CH_3)_2$, prolylethylamide, and D-alanylamide.

3. The compound of claim 1 wherein $Xaa_4$ is arginyl.

4. The compound of claim 3 wherein $Xaa_2$ is selected from the group consisting of norvalyl and D-norvalyl.

5. The compound of claim 4 selected from the group consisting of
N-Ac-Nva-Ile-Arg-Pro-NHCH$_2$CH$_3$ (SEQ ID NO:2);
N-(6-methylnicotinyl)-Nva-Ile-Arg-Pro-NHCH$_2$CH$_3$ (SEQ ID NO:4);
N-Ac-Nva-D-Ile-Arg-Pro-NHCH$_2$CH$_3$;
N-Ac-D-Nva-Ile-Arg-Pro-NHCH$_2$CH$_3$;
N-Ac-Nva-Ile-Arg-Pro-D-AlaNH$_2$;
N-Ac-Nva-Lys(Ac)-Arg-Pro-NHCH$_2$CH$_3$; (SEQ ID NO:16)
N-Ac-Nva-Ile-Arg-Pro-NHCH(CH$_3$)$_2$; (SEQ ID NO:18)
N-Ac-D-Nva-Ile-Arg-NHCH$_2$CH$_3$; and
N-Ac-Nva-Lys(Ac)-Arg-NHCH$_2$CH$_3$.

6. The compound of claim 3 wherein $Xaa_2$ is selected from the group consisting of glutaminyl, D-glutaminyl, leucyl, norleucyl, D-seryl, and seryl.

7. The compound of claim 6 selected from the group consisting of
N-Ac-Gln-Ile-Arg-Pro-NHCH$_2$CH$_3$ (SEQ ID NO:3);
N-Ac-Ser-Ile-Arg-Pro-NHCH$_2$CH$_3$ (SEQ ID NO:5);
N-Ac-Nle-Ile-Arg-Pro-NHCH$_2$CH$_3$ (SEQ ID NO:6);
N-Ac-Gln-Ile-Arg-Pro-D-AlaNH$_2$;
N-Ac-Leu-Ile-Arg-Pro-NHCH$_2$CH$_3$ (SEQ ID NO:7);
N-Ac-Ser-Ile-Arg-Pro-D-AlaNH$_2$;
N-Ac-Gln-Ile-Arg-NHCH$_2$CH$_3$;
N-Ac-Ser-Cit-Arg-Pro-NHCH$_2$CH$_3$; (SEQ ID NO:15)
N-Ac-D-Gln-Ile-Arg-Pro-D-AlaNH$_2$;

N-Ac-Gln-Ile-Arg-Pro-NHCH(CH$_3$)$_2$; (SEQ ID NO:19)
N-Ac-D-Gln-Ile-Arg-Pro-NHCH$_2$CH$_3$; and
N-Ac-D-Ser-Ile-Arg-NHCH$_2$CH$_3$.

8. The compound of claim 3 wherein Xaa$_2$ is selected from the group consisting of allothreonyl, allylglycyl, arginyl, glycyl, lysyl(N-epsilon acetyl), threonyl, D-tryptyl, and tryptyl.

9. The compound of claim 8 selected from the group consisting of
N-Ac-Lys(Ac)-Ile-Arg-Pro-NHCH$_2$CH$_3$ (SEQ ID NO:8);
N-Ac-Gly-Ile-Arg-Pro-NHCH$_2$CH$_3$ (SEQ ID NO:9);
N-Ac-alloThr-Ile-Arg-Pro-NHCH$_2$CH$_3$ (SEQ ID NO: 10);
N-Ac-alloThr-D-Ile-Arg-Pro-NHCH$_2$CH$_3$;
N-Ac-Trp-Ile-Arg-Pro-NHCH$_2$CH$_3$ (SEQ ID NO:11);
N-Ac-Trp-Ile-Arg-Pro-D-AlaNH$_2$;
N-Ac-Thr-Ile-Arg-Pro-D-AlaNH$_2$;
N-Ac-Thr-D-Ile-Arg-Pro-D-AlaNH$_2$;
N-Ac-Thr-Pro-Arg-Pro-NHCH$_2$CH$_3$; (SEQ ID NO:12)
N-Ac-Allylgly-Ile-Arg-Pro-NHCH$_2$CH$_3$; (SEQ ID NO:13)
N-Ac-D-Trp-Ile-Arg-Pro-NHCH$_2$CH$_3$;
N-Ac-Arg-Ile-Arg-Pro-NHCH$_2$CH$_3$; (SEQ ID NO:14)
N-Ac-Lys(Ac)-Ile-Arg-NHCH$_2$CH$_3$;
N-Ac-Thr-Ile-Arg-NHCH$_2$CH$_3$; and
N-Ac-Trp-Pro-Arg-NHCH$_2$CH$_3$.

10. The compound of claim 1 wherein Xaa$_5$ is arginyl.

11. The compound of claim 10 wherein Xaa$_2$ is beta-alanyl.

12. The compound of claim 11 that is N-Ac-bAla-Nva-Ile-Arg-Pro-NHCH$_2$CH$_3$; (SEQ ID NO:17).

13. A pharmaceutical composition comprising a compound of claim 1, or a therapeutically acceptable salt thereof, in combination with a therapeutically acceptable carrier.

* * * * *

UNITED STATES PATENT AND TRADEMARK OFFICE
CERTIFICATE OF CORRECTION

PATENT NO. : 7,037,897 B2 Page 1 of 1
APPLICATION NO. : 10/283813
DATED : May 2, 2006
INVENTOR(S) : Fortuna Haviv et al.

It is certified that error appears in the above-identified patent and that said Letters Patent is hereby corrected as shown below:

Col. 35, line 25
replace "R (CH2)nC(O) wherein n is an integer"
with --R-$(CH_2)_n$-C(O)-, wherein n is an integer--.

Col. 35, line 33
replace "omithyl"
with --ornithyl--.

Col. 36, line 46
replace "NIICII$_2$CII"
with --NHCH$_2$CH$_3$--.

Col. 37, line 15
replace "NIICII$_2$CII$_3$"
with --NHCH$_2$CH$_3$--.

Signed and Sealed this

Twenty-sixth Day of June, 2007

JON W. DUDAS
*Director of the United States Patent and Trademark Office*